United States Patent [19]

Partenheimer

[11] 4,242,128

[45] Dec. 30, 1980

[54] REMOVAL OF DISSOLVED COPPER FROM AQUEOUS SOLUTION ALSO CONTAINING DISSOLVED COBALT OR MANGANESE

[75] Inventor: Walter Partenheimer, Naperville, Ill.

[73] Assignee: Standard Oil Company (Indiana), Chicago, Ill.

[21] Appl. No.: 3,366

[22] Filed: Jan. 15, 1979

[51] Int. Cl.³ .............................................. C22B 15/12
[52] U.S. Cl. ........................................ 75/109; 75/117; 75/119; 75/121
[58] Field of Search ................. 75/109, 117, 119, 121

[56] References Cited

U.S. PATENT DOCUMENTS

| | | | |
|---|---|---|---|
| 3,341,470 | 9/1967 | Hensley | 252/412 X |
| 3,586,498 | 6/1971 | Kasey | 75/109 X |
| 4,016,055 | 4/1977 | Gandon et al. | 75/109 X |
| 4,149,945 | 4/1979 | Kust | 75/117 X |
| 4,152,142 | 5/1979 | Schlitt et al. | 75/117 X |

*Primary Examiner*—G. Ozaki
*Attorney, Agent, or Firm*—Fred R. Ahlers; William H. Magidson; William T. McClain

[57] ABSTRACT

This invention relates to the selective removal of dissolved copper from an aqueous solution also containing dissolved cobalt, or manganese or cobalt and manganese with other extraneous metals such as iron, nickel and chromium and more particularly pertains to such removal of copper where its content and the respective contents of iron, nickel and chromium are a small fraction of; e.g., from 0.01 to 0.1 times, the concentration of cobalt, and manganese if present can be in a concentration from 2 up to 10 times the concentration of cobalt.

1 Claim, No Drawings

REMOVAL OF DISSOLVED COPPER FROM AQUEOUS SOLUTION ALSO CONTAINING DISSOLVED COBALT OR MANGANESE

BACKGROUND OF THE INVENTION

Aqueous solutions of cobalt or cobalt and manganese also containing dissolved extraneous contaminant metals copper, iron, nickel and chromium can be obtained from the aqueous extraction of residues from the production of ortho-, iso- or terephthalic acid by liquid phase oxidation of the corresponding xylene isomer with air in the presence of cobaltous ions or mixture of cobaltous and manganous ions. The residues extracted result from the recovery of the phthalic acid from the oxidation effluent and, if a solvent is used, the evaporation of the reaction solvent. The extraneous contaminant metals copper, iron, nickel and chromium have at different concentrations on cobalt adverse effects on the catalysis. For example, a copper concentration of 800 ppm of copper on cobalt substantially retards the oxidation of o-xylene while a 5000 ppm concentration of iron or nickel on cobalt has no adverse effect for o-xylene oxidation.

It is known that copper can be precipitated from such aqueous solutions (e.g., from U.S. Pat. No. 3,341,470) by treatment of the solution with hydrogen sulfide, a rather poisonous gas.

We have now discovered a less hazardous process for removing copper from such solution by a simple flow process. Such process is valuable for the removal of copper from aqueous solutions of cobalt wherever obtained.

STATEMENT OF THE INVENTION

Dissolved copper is readily and simply removed from an aqueous solution containing dissolved cobalt or manganese or cobalt and manganese by contacting the solution at a slightly acidic pH, e.g. a pH of from 5.8 up to 6.5, with particulated iron such as iron filings or shavings or cuttings or powder for more than 30 minutes but less than 120 minutes and then separating the solution from the particulated iron. Such removal of copper also removed about 5.4% of the cobalt, 16% of the manganese and from 50 to 60% of the chromium present.

To demonstrate the effectiveness of the present invention an aqueous solution containing cobalt, chromium, copper, iron, manganese, and nickel is contained and vigorously stirred with iron filings in the proportion of 5.00 grams of iron per 140 grams of solution where pH has been adjusted to 6.0 from 2.65 by the addition of sodium hydroxide. The solution was filtered to remove precipitate formed upon said adjustment. Samples of the solution are taken periodically after contact of the solution with the iron. The samples are analyzed for their metals content. The results of such analyses are shown in the table to follow wherein the analysis at 0 minutes is the filtrate solution after pH adjustment.

The technical effect of the present inventive process for copper removal from solutions to plate out the copper on the iron particulates.

| Metals ppm | Minutes After Contact With Iron | | | | | | |
|---|---|---|---|---|---|---|---|
| | 0 | 30 | 60 | 120 | 180 | 300 | 1275 |
| Co | 2970 | 2830 | 2810 | 2830 | 2770 | 2780 | 1760 |
| Cr | 27 | 14 | 11 | 13 | 9 | 12 | 1 |
| Cu | 10.7 | 2.6 | 0.1 | 1.0 | 1.4 | 1.2 | 0.9 |
| Fe | 264 | 240 | 290 | 670 | 128 | 410 | 730 |
| Mn | 7482 | 6300 | 6400 | 6300 | 6300 | 6600 | 6500 |
| Ni | 290 | 300 | 310 | 325 | 325 | 300 | 147 |

The invention claimed is:

1. The method of decreasing the concentration of dissolved copper in an aqueous solution obtained from the aqueous extraction of a residue from the production of a phthalic acid product by the liquid phase oxidation of a xylene with air in the presence of cobaltous ion or mixtures of cobaltous and manganous ions in the presence or absence of reaction solvent wherein said residue remains after recovery of the phthalic acid product and, if used, separation of reaction solvent; wherein said extract solution contains mainly dissolved cobalt or cobalt and manganese together with a small fraction thereof of the contaminant metals copper, iron, nickel and chromium as their phthalates; and wherein the concentration of dissolved copper is at or above 800 weight parts per million weight parts of cobalt; which copper decreasing method comprises adjusting the pH of such solution to a pH between 5.8 and 6.5, contacting such pH adjusted solution with particulates of iron in an amount thereof of five weight parts for each 140 weight parts of solution for at least 30 minutes but less than 120 minutes and thereafter separating the solution from the iron particulates.

* * * * *